(12) United States Patent
Lin et al.

(10) Patent No.: US 8,530,242 B2
(45) Date of Patent: Sep. 10, 2013

(54) WAFER PROCESS CHAMBER LEAK DETECTOR

(75) Inventors: George Lin, Shan-Hua Township, Tainan County (TW); Ming-Hsiung Fu, Jhubei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 902 days.

(21) Appl. No.: 12/414,373

(22) Filed: Mar. 30, 2009

(65) Prior Publication Data

US 2010/0248382 A1 Sep. 30, 2010

(51) Int. Cl.
*G01N 21/00* (2006.01)

(52) U.S. Cl.
USPC ............... 436/164; 137/551; 73/40; 73/198; 438/5

(58) Field of Classification Search
None
See application file for complete search history.

(56) References Cited

U.S. PATENT DOCUMENTS

2007/0181192 A1* 8/2007 Choi et al. .................. 137/551

OTHER PUBLICATIONS

Crystec Technology Trading GmbH, Plasma Etcher, 2007, retrieved from internet site: http://web.archive.org/web/20070928042110/ http://www.crystec.com/trietche.htm.*
Russell, A.P., et al. Optical sensor for the determination of moisture, 1985, Analytica Chimica Acta, vol. 170, pp. 209-216.*

\* cited by examiner

*Primary Examiner* — Robert Xu
(74) *Attorney, Agent, or Firm* — Haynes and Boone, LLP

(57) ABSTRACT

The present disclosure includes a method for monitoring leaks in a wafer process chamber. The method includes providing a wafer process chamber coupled to a gas supply by a gas supply line, wherein an indicator member is coupled to the gas supply line between the gas supply and the wafer process chamber, and a final valve is located on the gas supply line between the gas supply and the indicator member. A gas is supplied from the gas supply to the wafer process chamber through the gas supply line. A light is emitted and directed through the indicator member. The light that was directed through the indicator member is then reflected using a reflecting member. The reflected light is then received and compared to the light emitted in order to determine that the color of the indicator member has changed and a leak has been detected in the gas supply line.

14 Claims, 10 Drawing Sheets

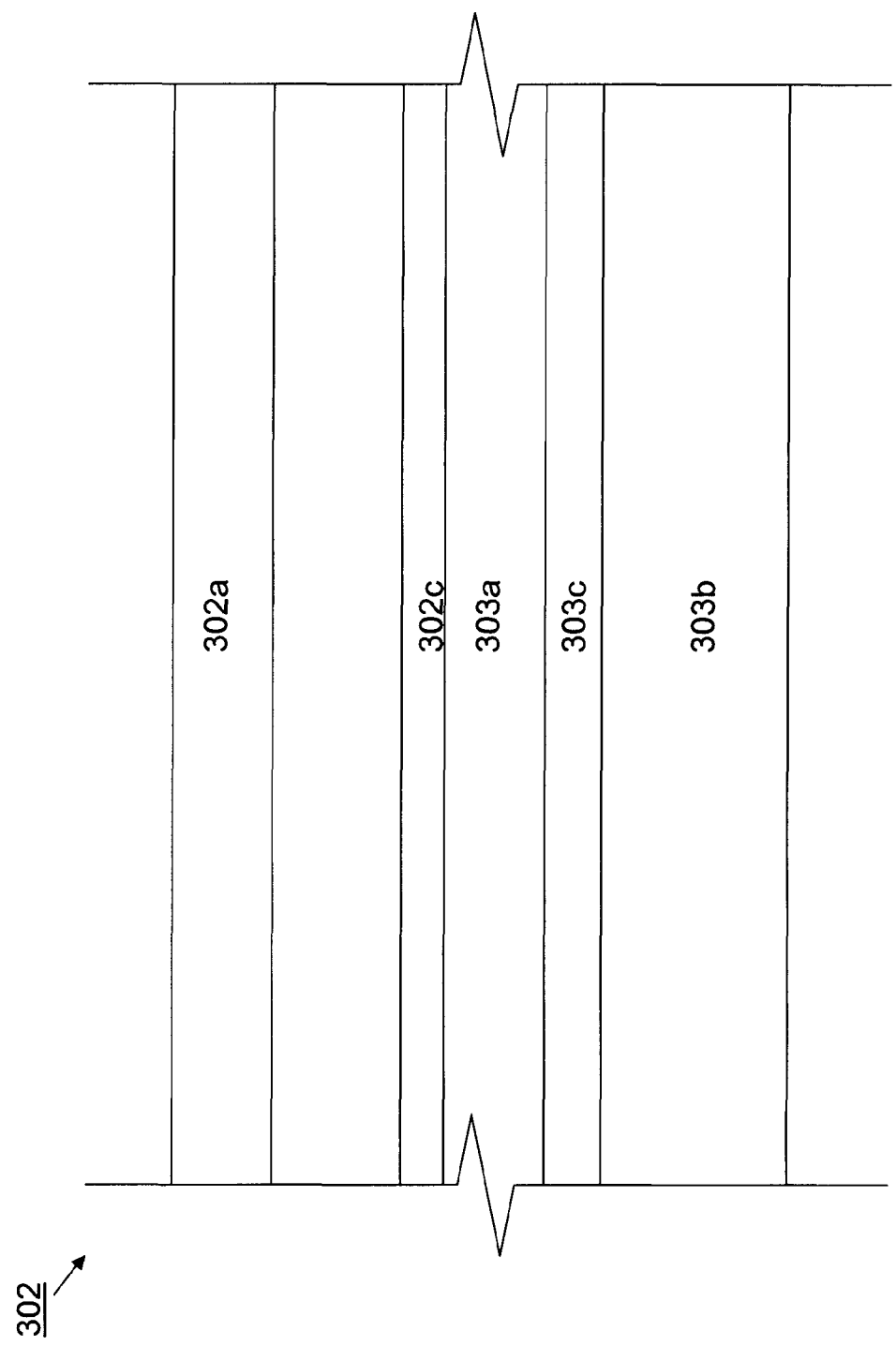

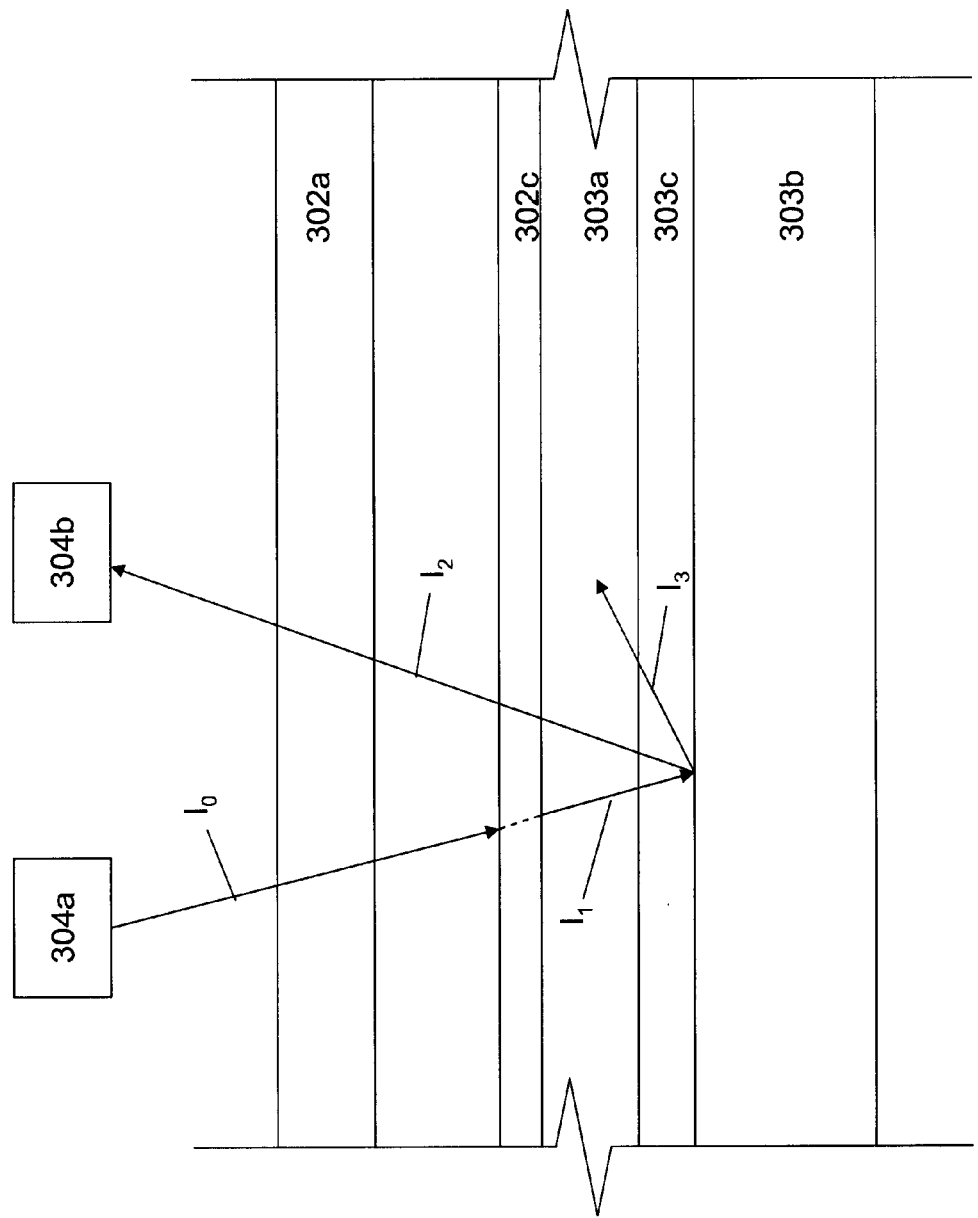

US 8,530,242 B2

WAFER PROCESS CHAMBER LEAK DETECTOR

BACKGROUND

The present disclosure relates generally to integrated circuit manufacturing processes and in particular to a wafer process chamber leak detector for detecting leaks in the integrated circuit manufacturing process.

In integrated circuit manufacturing processes, an inert gas may routed into the wafer process chamber and to the wafer in order to cool the wafer during manufacturing. In most cases, the environment outside of the wafer process chamber will contain moisture. If there is a leak in the inert gas supply line to the wafer process chamber, that moisture may enter the inert gas supply line and, subsequently, the wafer process chamber. This can result in several negative consequences such as, for example, the scrapping of one or more wafer lots, polymer formation in the wafer process chamber, and/or a variety of other negative consequences known in the art.

SUMMARY

A wafer process chamber leak detector includes a wafer process chamber. A gas supply line couples a gas supply to the wafer process chamber. The gas supply line includes a final valve located on the gas supply line between the gas supply and the wafer process chamber. An indicator member is coupled to the gas supply line between the final valve and the wafer process chamber. A reflecting member is located adjacent the indicator member. A signal amplifier is operable to direct a light through the indicator member in order to be reflected off the reflecting member such that the reflected light is received by the signal amplifier.

Another wafer process chamber leak detector is provided. The wafer process chamber leak detector includes a wafer process chamber for housing a wafer support device. A gas supply line couples a gas supply to the wafer support device and is operable to supply a gas to a wafer located on the wafer support device. An indicator member is coupled to the gas supply line between the gas supply and the wafer support device. A final valve is located on the gas supply line between the gas supply and the indicator member, where there are no valves located on the gas supply line between the final valve and the indicator member and there are no valves located on the gas supply line between the indicator member and the wafer support device. A reflecting member is located adjacent the indicator member. An emitter is operable to direct a light through the indicator member in order to be reflected off the reflecting member. A receiver is operable to receive the light that is reflected off the reflecting member.

Also provided is a method for monitoring leaks in a wafer process chamber. The method includes providing a wafer process chamber coupled to a gas supply by a gas supply line, where an indicator member is coupled to the gas supply line between the gas supply and the wafer process chamber, and a final valve is located on the gas supply line between the gas supply and the indicator member; supplying a gas from the gas supply to the wafer process chamber through the gas supply line; emitting a light and directing the light through the indicator member; reflecting the light that was directed through the indicator member using a reflecting member; and receiving the reflected light and comparing the reflected light received to the light emitted in order to determine that the color of the indicator member has changed and a leak has been detected in the gas supply line.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 3b is a schematic view illustrating an embodiment of a leak indicator used with the wafer process chamber leak detector of FIG. 3a;

FIG. 3c is a schematic view illustrating an embodiment of a signal amplifier used with the wafer process chamber leak detector of FIG. 3a;

FIG. 6b is a schematic view illustrating an embodiment of an indicator member in the leak indicator of FIG. 3b being monitored for a color change.

DETAILED DESCRIPTION

Figure 1:
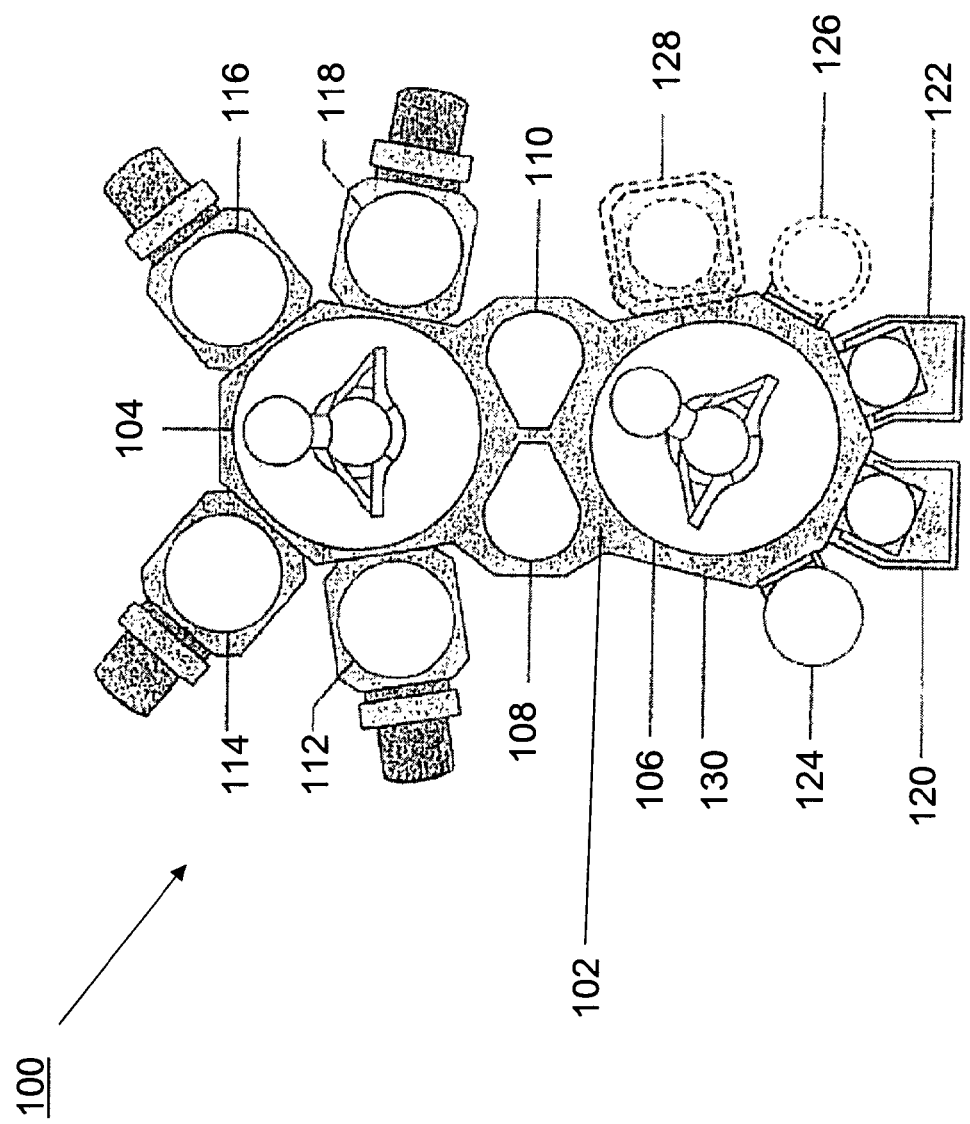
FIG. 1 is a top view illustrating an embodiment of a multi-chamber process tool.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring now to FIG. 1, a multi-chamber process tool 100 is illustrated. In an embodiment, the multi-chamber process tool 100 allows a number of sequential process steps to be carried out on a wafer without exposing the wafer to the atmosphere. The multi-chamber process tool 100 includes a base 102 having a high-vacuum transfer chamber 104, a buffer-transfer chamber 106, a pre-clean chamber 108, and a cool-down chamber 110. A plurality of wafer process chambers 112, 114, 116, and 118 are coupled to the base 102 and located adjacent the transfer chamber 104. In an embodiment, the wafer process chamber chambers 112, 114, 116, and 118 are chambers including wafer processing devices for processing a wafer using techniques such as, for example, sputtering and/or a variety of other processing techniques known in the art. A plurality of cassette loadlocks 120 and 122 are coupled to the base 102 adjacent each other and the buffer chamber 106. A de-gas/wafer orienting chamber 124 is coupled to the base 102 adjacent the cassette loadlock 120 and the buffer chamber 106. A cool-down chamber 126 is coupled to the base 102 adjacent the cassette loadlock 122 and the buffer chamber 106. A metal anneal chamber 128 is coupled to the base 102 adjacent the cool-down chamber 126 and the buffer chamber 106. An expansion slot 130 is located on the base 102 and operable to couple a chamber (not illustrated) or other processing device to the base 102. One of skill in the art will recognize that a variety of different processing devices may be added to the base and/or replace the processing devices illustrated in FIG. 1. In operation, the buffer-transfer chamber 106 may receive wafers from the cassette loadlock 120, and then sequentially feed the wafers to the de-gas/wafer orienting chamber 124 and the pre-clean chamber 108. The high-vacuum transfer chamber 104 then may receive the wafers from the pre-clean chamber 108 and transfer the wafers to the wafer process chambers 112, 114, 116, and/or 118, as needed, and then deliver the wafers to the cool-down chamber 110. The buffer-transfer chamber 106 then may transfer the wafers from the cool-down chamber 110 to the cassette loadlock 122. In an embodiment, the buffer transfer chamber 106 may sequentially feed the wafers to the metal anneal chamber 128 and cool-down chamber 126, respectively, before delivering the wafers to the loadlock 122.

Figure 2:
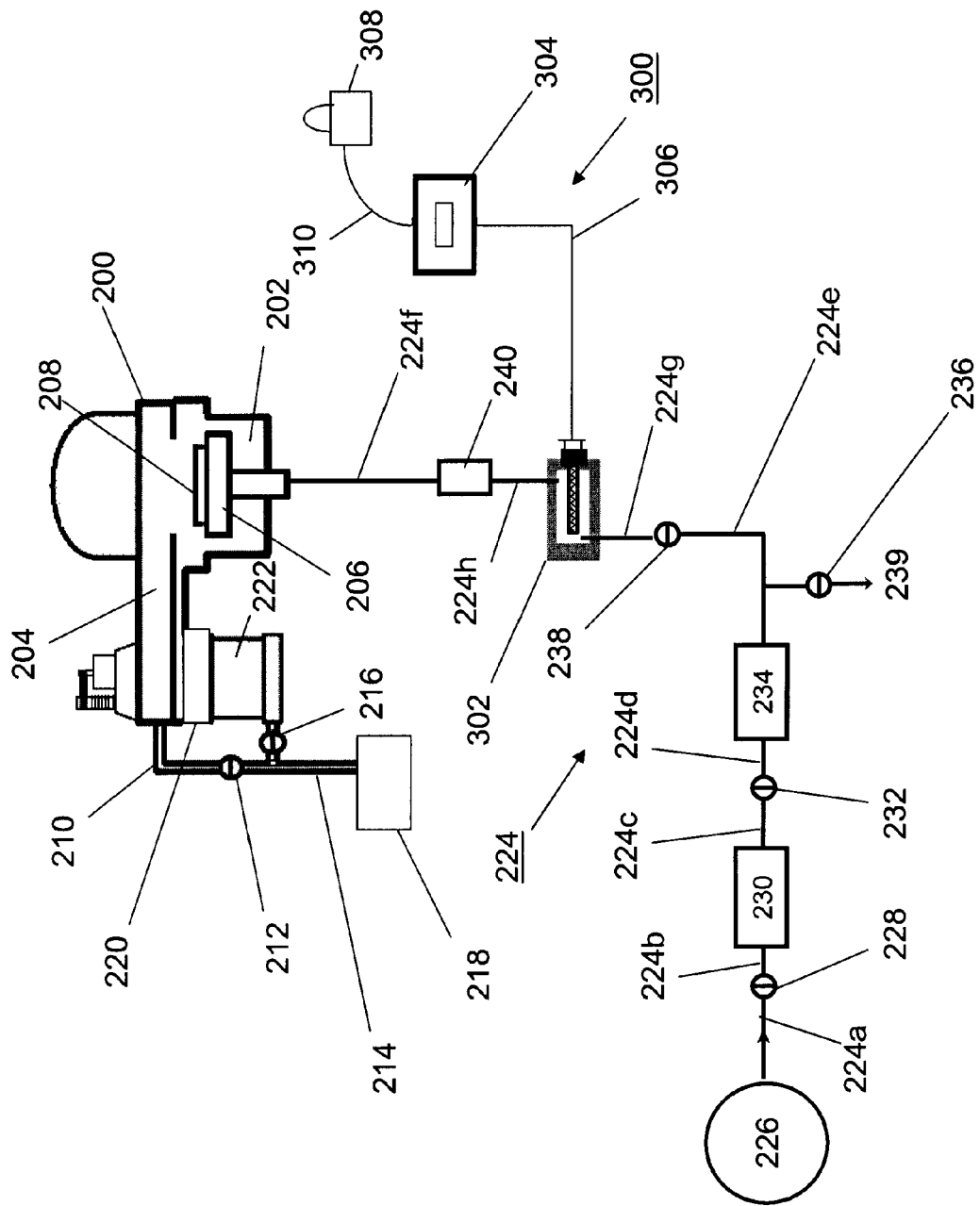
FIG. 2. is a schematic view illustrating an embodiment of a wafer process chamber used with the multi-chamber process tool of FIG. 1.

Referring now to FIG. 2, a wafer process chamber 200 including a wafer process chamber leak detector is illustrated. In an embodiment, the wafer process chamber 200 may be one or more of the wafer process chambers 112, 114, 116, and 118 described above with reference to FIG. 1. In the illustrated embodiment, the wafer process chamber 200 includes a lower chamber 202 and an upper chamber 204. The lower chamber 202 of the wafer process chamber 200 houses a wafer support device 206 that supports a wafer 208. In an embodiment, the wafer support device 206 may include a cathode and/or a variety of other wafer support and/or processing devices known in the art. In the illustrated embodiment, a rough line 210 extends from the upper chamber 204 of the wafer process chamber 200 and includes a rough line valve 212. A forline 214 extends from the rough line valve 212 and includes a forline iso-valve 216. A dry pump 218 is also coupled to the forline 214. A gate valve 220 is coupled to the lower chamber 202 of the wafer process chamber 200, and a turbo pump 222 is located between the gate valve 220 and the forline iso-valve 216. While the wafer process chamber 200 has been illustrated and described as including specific components, one of skill in the art will recognize that some or all of the components in the illustrated embodiment may be removed and/or a variety of different components may supplement or replace those components without departing from the scope of the present disclosure.

A gas supply line 224 extends between the wafer process chamber 200 and a gas supply 226. In an embodiment, the gas supply 226 includes a helium gas. However, in alternative embodiment, the gas supply may include inert gases such as, for example, Argon, Nitrogen, and/or a variety of other inert gasses known in the art. A first section 224a of the gas supply line 224 extends between the gas supply 226 and a manual valve 228. A second section 224b of the gas supply line 224 extends between the manual valve 228 and a mass flow meter 230. A third section 224c of the gas supply line 224 extends between the mass flow meter 230 and a supply valve 232. A fourth section 224d of the gas supply line 224 extends between the supply valve 232 and a universal pressure control 234. A fifth section 224e of the gas supply line 224 extends between the universal pressure control 234 and each of a dump valve 236 and a final valve 238. The dump valve 236 is coupled to a pumping line 239. An eighth section 224f of the gas supply line 224 extends between the wafer support device 206 in the wafer process chamber 200 and a filter 240. A sixth section 224g of the gas supply line 224 extends from the final valve 238. A seventh section 224h of the gas supply line 224 extends from the filter 240. A wafer process chamber leak detector 300, illustrated in FIG. 3a and described in more detail below, is coupled the sixth section 224g and the seventh section 224h of the gas supply line 224.

Figure 3A:
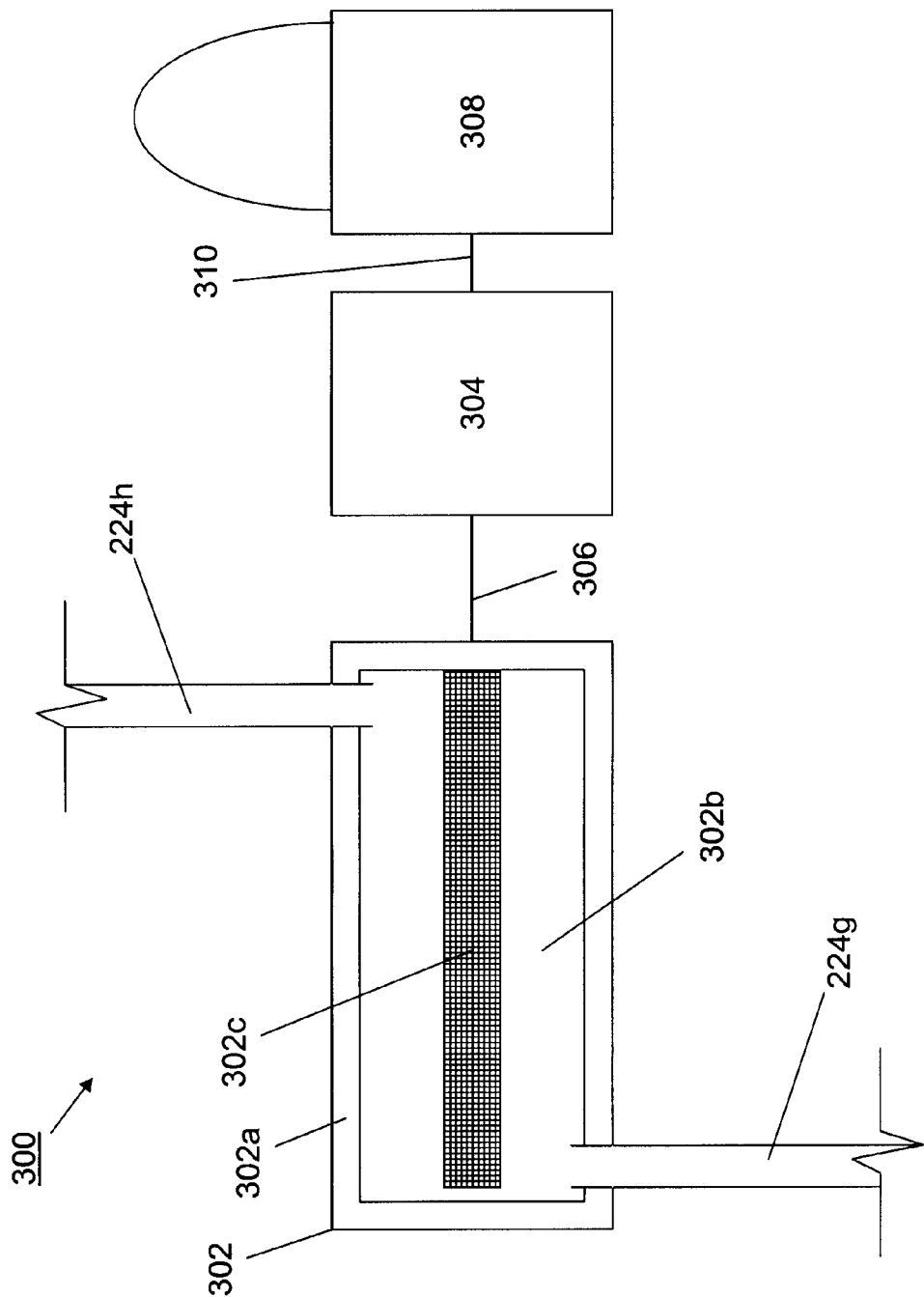
FIG. 3a is a schematic view illustrating an embodiment of a wafer process chamber leak detector used with the wafer process chamber of FIG. 2.

Referring now to FIGS. 2 and 3a, the wafer process chamber leak detector 300 includes a leak indicator 302 that is coupled to the sixth section 224g and the seventh section 224h of the gas supply line 224. A signal amplifier 304 is coupled to the leak indicator 302 by a coupling 306. In an embodiment, the coupling 306 may include a coupling that is operable to transmit light such as, for example, an optical fiber. However, in other embodiment, the signal amplifier 304 may not be physically coupled to the leak indicator 302, as described in further detail below. A gas supply cut off device 308 is coupled to the signal amplifier 304 by a coupling 310.

In an embodiment, the leak indicator 302 includes a base 302a defining a cavity 302b that houses an indicator member 302c. In an embodiment, the indicator member 302c includes a Cobalt(II) Chloride [CoCl$_2$(H$_2$O)$_2$] indicator that is operable to change color due to an interaction with water according to the reaction:

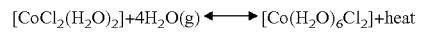

[CoCl$_2$(H$_2$O)$_2$]+4H$_2$O(g) ⇌ [Co(H$_2$O)$_6$Cl$_2$]+heat

In an embodiment using Cobalt(II) Chloride, the color of the indicator member 302c changes from a blue color in the absence of water to a red/pink color in the presence of water. However, one of skill in the art will recognize that a variety of other indicator members such as, for example, Copper Sulfate (which is a white color as [CuSO$_4$] and changes to a blue color as [CuSO$_4$*5H$_2$O]), may be substituted for the Cobalt(II) Chloride indicator member without departing from the scope of the present disclosure. In experimental embodiments, Cobalt(II) Chloride was found to possess a high response time ($\sim$1/10$^5$ seconds), stability at room temperature, and re-usability (e.g., as seen in the equation above, the application of heat to [Co(H$_2$O)$_6$Cl$_2$] returns the indicator member to [CoCl$_2$(H$_2$O)$_2$].)

Referring now to FIG. 3b, in an embodiment, the base 302a of the leak indicator 302 may be a quartz tube. However, in an embodiment, the base 302a may include a variety of transparent materials known in the art. The indicator member 302c may be a layer of Cobalt(II) Chloride having a thickness of approximately 1 μm that is deposited on a filter paper 303a having a thickness of approximately 0.15 mm. The filter paper 303a may be coupled to a reflecting member 303b such as, for example, a mirror or other reflecting member known in the art, using a layer of adhesive 303c such as, for example, mucilage or another adhesive known in the art.

Figure 3C:
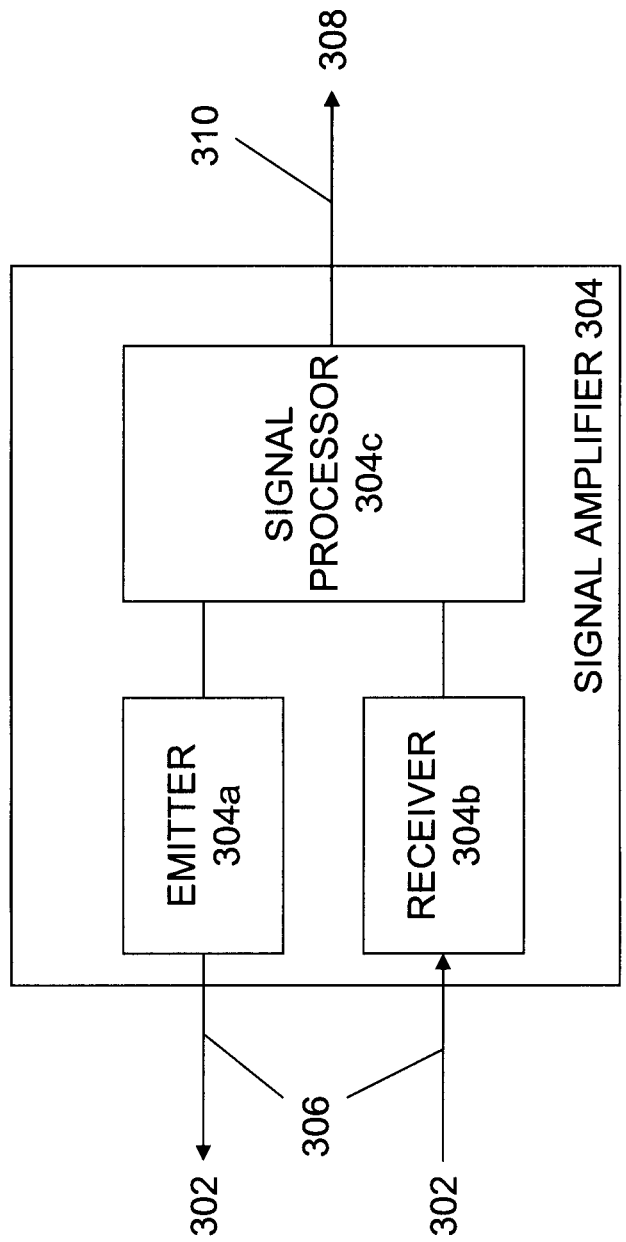
Figure 4:
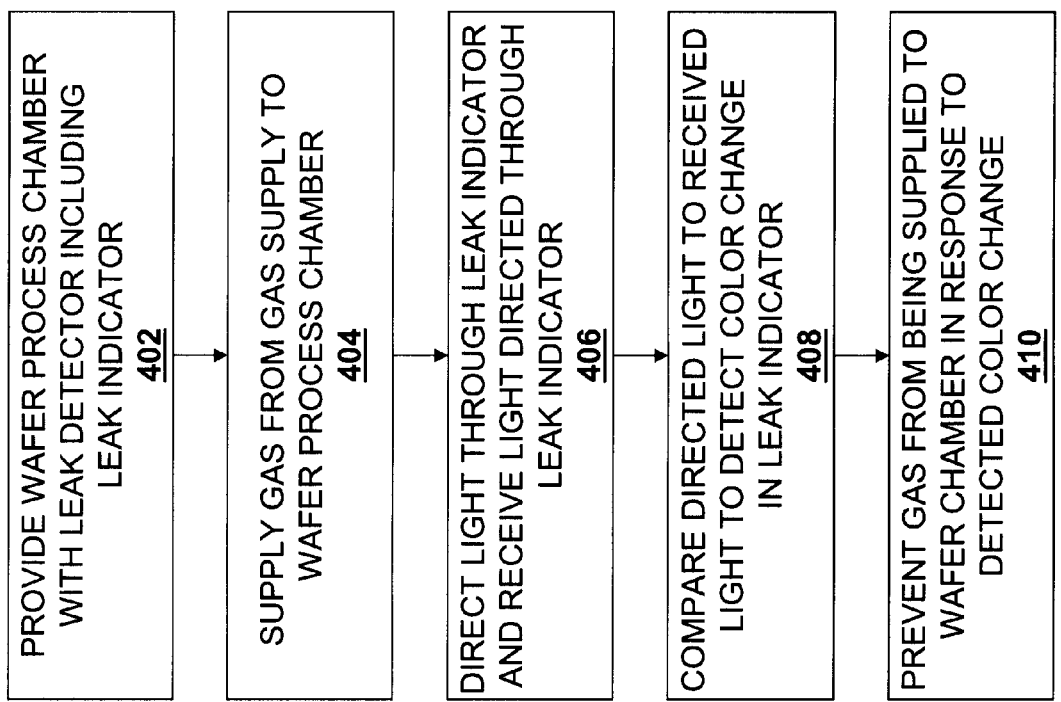
FIG. 4 is a flow chart illustrating of an embodiment of method for monitoring leaks in a wafer process chamber.

Referring now to FIGS. 2, 3a, and 3c, the sixth section 224g of the gas supply line 224 is coupled to the cavity 302a such that it may supply gas from the gas supply 226 to the cavity 302a, and the seventh section 224h of the gas supply line 224 is coupled to the cavity 302a such that it may transmit gas from the cavity 302a to the wafer process chamber 200. The signal amplifier 304 includes an emitter 304a that is operable to emit a light such that the light may be directed towards the indicator member 302c via the coupling 306. The signal amplifier 304 also includes a receiver 304b that is operable receive a light via the coupling 306. A signal processor 304c is coupled to each of the emitter 304a and the receiver 304b. In an embodiment, the signal processor 304c may also be coupled to the gas supply cut off device 308 through the coupling 310.

Referring now to FIGS. 2, 3a, 3b, 3c, 4, and 5, a method 400 for monitoring a leak in a wafer process chamber is illustrated. The method 400 begins at block 402 where a wafer process chamber with a leak detector including a leak indicator is provided. In an embodiment, the wafer process chamber 200 including the leak detector 300 having the leak indicator 302 is provided. In an embodiment, the wafer 208 is positioned in the wafer process chamber 200 on the wafer support device 206, and a wafer processing step is performed on a first side of the wafer 208 that is opposite the side of the wafer 208 that is in contact with the wafer support device 206.

The method 400 then proceeds to block 404 where gas from a gas supply is supplied to the wafer process chamber. In an embodiment, the dump valve 236 is closed while the manual valve 228, supply valve 232, and the final valve 238 are opened and, in response, gas under pressure in the gas supply 226 flows through the gas supply line 224, through the mass flow meter 230, the universal pressure control 234, the leak indicator 302, and the filter 240 until it enters the lower chamber 202 of the wafer process chamber 200 through the wafer support device 206. In an embodiment, the gas is supplied to a second side of the wafer 208 (which is in contact with the wafer support device 206 and opposite the first side of the wafer 208 upon which a wafer processing step is being performed) through the wafer support device 206 in order to cool the wafer 208 during processing, after which the gas enters the lower chamber 202 of the wafer process chamber 200.

Figure 5:
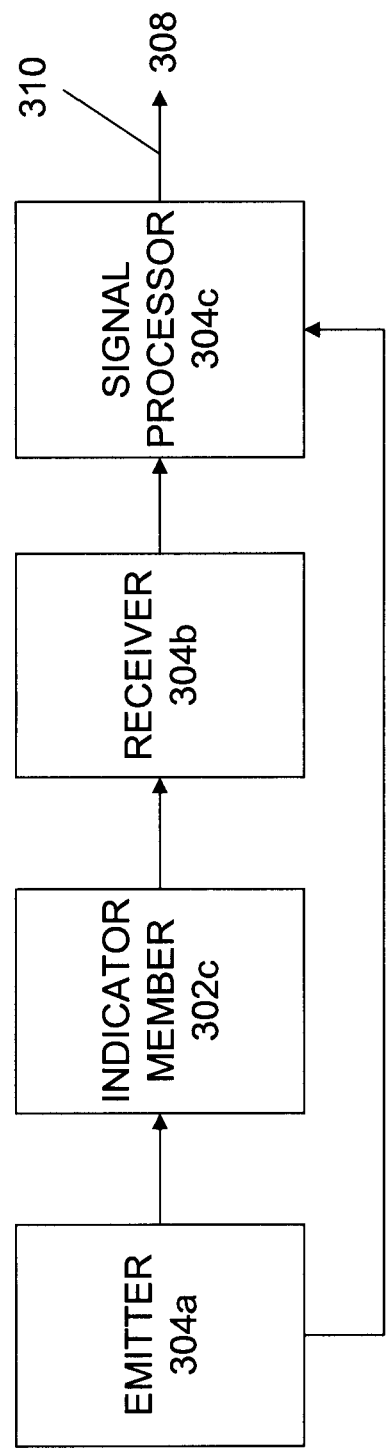
FIG. 5 is a schematic view illustrating an embodiment of the signal amplifier of FIG. 3c monitoring for a color change in an indicator member.

The method 400 then proceeds to block 406 where light is directed through a leak indicator and the light directed through the leak indicator is received. As illustrated in FIG. 5, the emitter 304a may emit a light that is directed through the indicator member 302c. In passing through the indicator member 302c, the intensity of the light will change. The light that passes through the indicator member 302c is then received by the receiver 304b. In an embodiment, the light emitted from the emitter 304a may be directed through the indicator member 302c by the coupling 306 using, for example, one or more optical fibers, and the light may be returned to the receiver 304b via the coupling 306 using, for example, the same or other optical fibers. However, the light emitted by the emitter 304a and received by the receiver 304b need not be directed by a physical coupling, as will be described in further detail below.

The method 400 then proceeds to block 408 where the directed light from the emitter is compared to the received light at the receiver in order to detect a color change in the leak indicator. In an experimental embodiment, the pressure in the wafer process chamber 200 was about 12 mTorr, the pressure in the gas supply line 224 was around 7-55 Torr, and the pressure outside the wafer process chamber 200 and the gas supply line 224 ("the wafer fabrication environment") was around 760 Torr. In addition, the wafer fabrication environment was about 40% water. Thus, if there is a leak in the gas supply line 224, water may enter the gas supply line 224 and be transmitted to the water process chamber 200. Due to the indicator member 302c being operable to change color due to a reaction with water, such a leak will cause the indicator member 302c in the leak indicator 302 to change color. In an embodiment, the signal processor 304c is operable to determine the intensity of the light directed by the emitter 304a at the indicator member 302b, and is also operable to determine the intensity of the light received by the receiver 304b. The signal processor 304c may compare the light emitted by the emitter 304a to the light received by the receiver 304b, and then produce a signal that may be interpreted to determine whether the indicator member 302b has changed color.

The method 400 then proceeds to block 410 where gas is prevented from being supplied to the wafer chamber in response to a detected color change in the indicator member. The signal produced by the signal processor 304c in response to the comparing of the light emitted by the emitter 304a with the light received by the receiver 304b is sent to the gas supply cut off device 308. The gas supply cut off device 308 is operable, in response to receiving a signal from the signal processor 304c that is indicative of a sufficient color change in the indicator member 302c, to prevent gas from being supplied to the wafer chamber 200. One of skill in the art will understand that a variety of color changes in the indicator member 302c may be sufficient to warrant the prevention of the gas into the wafer process chamber 200 depending on the situation in which the leak detector 300 is being used. The gas supply cut off device 308 may prevent gas supply to the wafer process chamber 200 by, for example, producing a warning light as an indicator to an operator of the wafer process chamber 200 to close the manual valve 228, automatically closing the supply valve 232 and/or the final valve 238, and/or opening the dump valve 236. As can be seen in FIG. 2, the final valve 238 is the last valve between the gas supply 226 and the wafer process chamber 200/wafer support device 206, and the leak indicator 302 is located on the gas supply line 224 between the final valve 238 and the wafer process chamber 200/wafer support device 206. By positioning the leak indicator 302 on the gas supply line 224 in such a manner, real-time monitoring of the wafer process chamber 200 for gas supply line leaks is provided, for when a leak in the gas-supply line 224 occurs, the resulting water entering the gas supply line 224 will react with the indicator member 302c, cause a color change in the indicator member 302c, and result in the gas supply cut off device 308 preventing gas from being supplied to the wafer process chamber 200/wafer support device 206. One of skill in the art will recognize this as one of a variety of advantages the present disclosure provides over conventional leak detection methods (e.g., moving a gas detector adjacent the gas supply line 224 or doing a leak rate test using a manometer.)

Figure 6A:
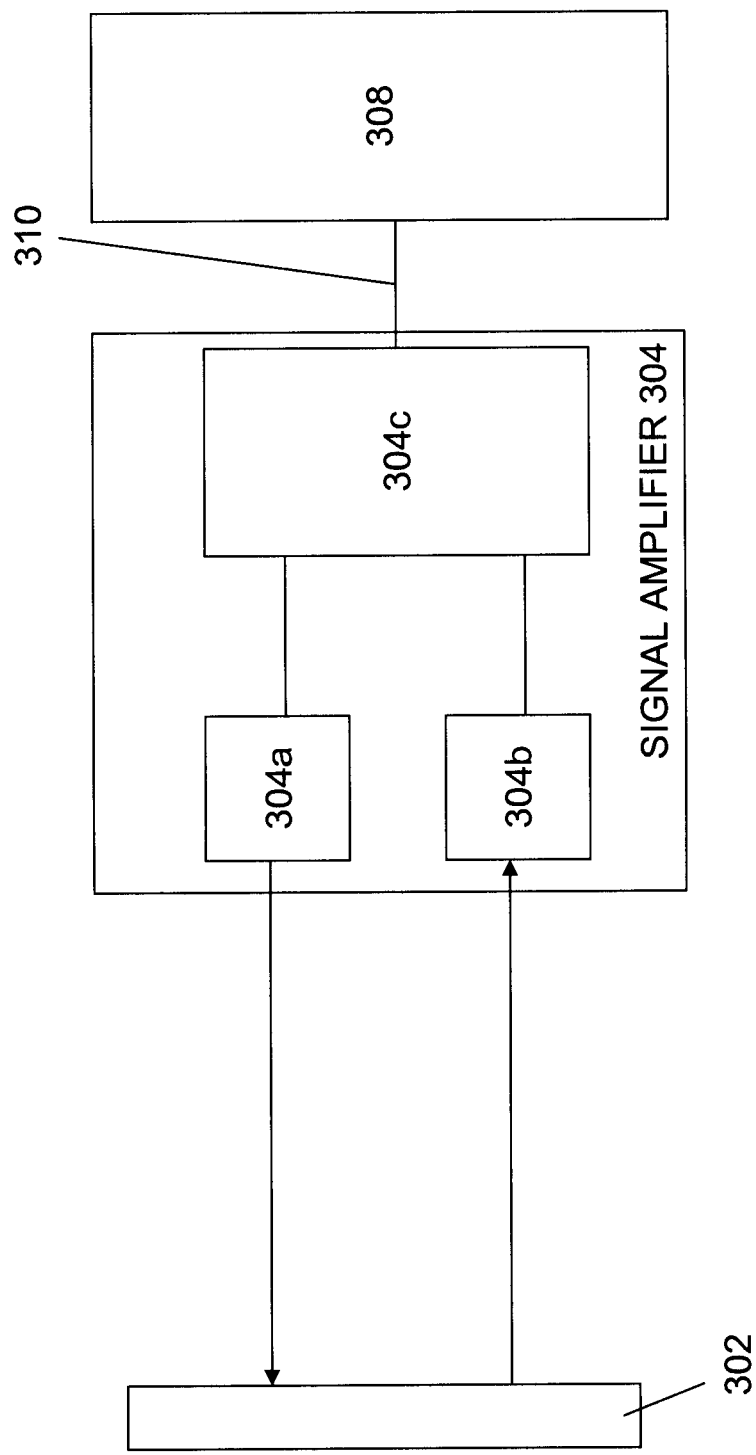
FIG. 6a is a schematic view illustrating an embodiment of the signal amplifier of FIG. 3c monitoring for a color change in a leak indicator.

Referring now to FIG. 6a and 6b, in an embodiment, at block 406 of the method 400, the emitter 304a may emit a light having an intensity $I_0$ that is then directed towards the leak indicator 302b. That light will pass through the indicator member 302c. Upon passing through the indicator member 302c, the light will have an intensity $I_1$. That light will then be reflected by the reflecting member 303b and a portion of that light having an intensity $I_2$ will be directed back through the indicator member 302c while a portion having an intensity $I_3$ will be scattered. The light that is directed back through the leak indicator 302c is then received by the receiver 304b. In experimental embodiments, it was found that the intensity $I_2$ of the light that is directed back through the indicator member 302c after it is reflected by the reflecting member 303b is very close to the intensity $I_1$ of the light after it first passes through the indicator member 302c due to the effects related to light scattering and the intensity loss through the other materials being relatively small. In an embodiment, the reflecting member 303b may reflect the light that first passes through the leak indicator 302b (i.e., the light having intensity $I_1$) directly to the emitter 304b rather than reflecting the light back through the indicator member 302c. As stated above, the light directed by the emitter 304a and received by the receiver 304b may at least partially be directed and received through a physical medium such as, for example, an optical fiber. However, as illustrated in FIG. 6b, the light directed from emitter 304a and received by the receiver 304b may not require a physical medium and rather may be directed through air, a vacuum, and/or other non-physical media known in the art, such that it passes through the base 302a (e.g., a quartz tube or other transparent material), is reflected, passes back through the base 302a, and is received.

Figure 7:
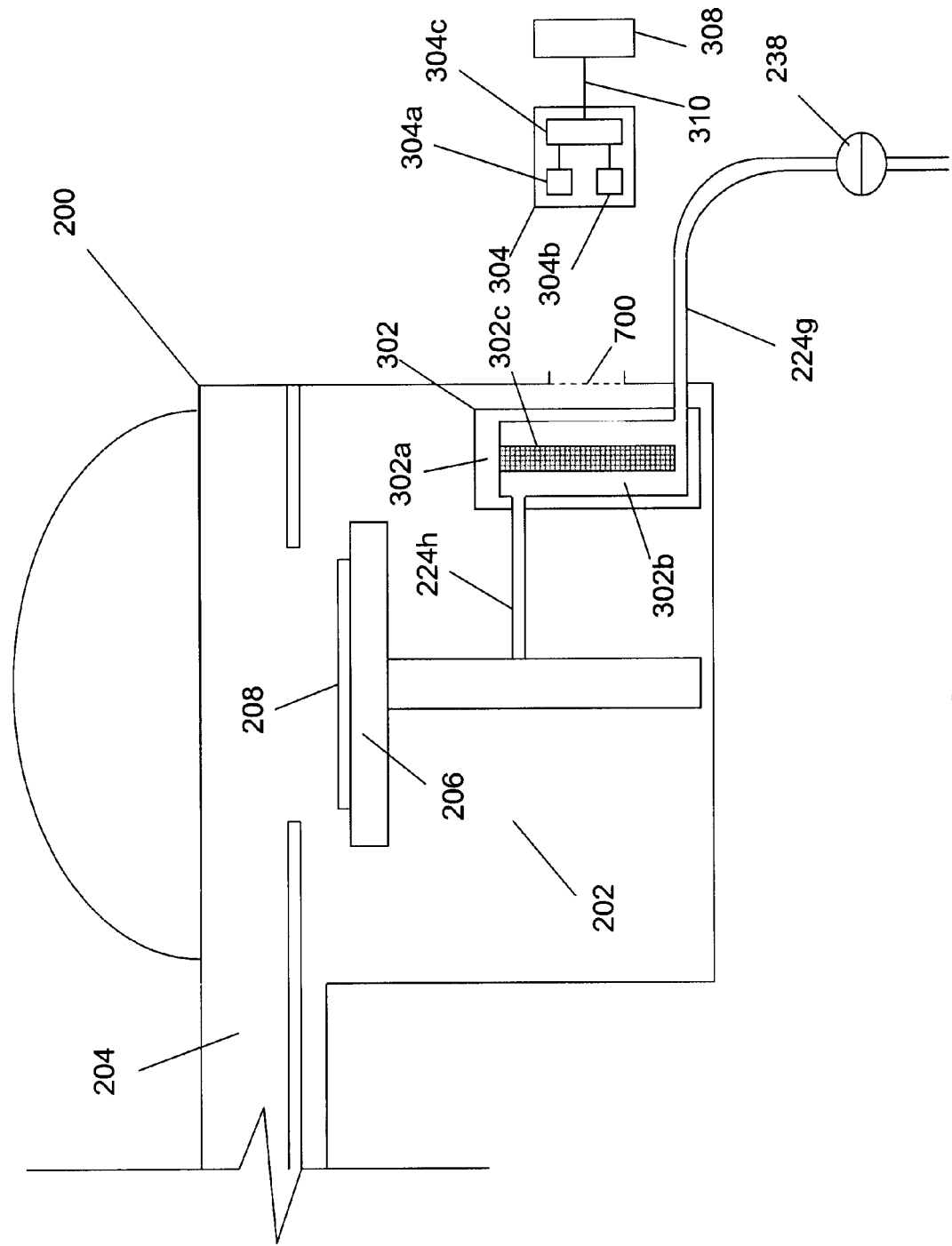
FIG. 7 is a schematic view illustrating an embodiment of the signal amplifier of FIG. 3c monitoring for a color change in a leak indicator.

For example, referring now to FIG. 7, in an embodiment, the leak indicator 302b is located in the lower chamber 202 of the wafer process chamber 200. However, one of skill in the art will recognize that the leak indicator 302 may be located in other positions in the wafer process chamber 200 such as, for example, the upper chamber 204 of the wafer process chamber 200. The wafer process chamber 200 includes a section 700 that allows light emitted from the emitter 304a to pass through the wafer process chamber 200 such that the light may reach the indicator member 302c and be reflected back to the receiver 304b. One of skill in the art will recognize one of the benefits of such an embodiment is that it allows the signal amplifier 304 to be separated from the leak indicator 302 and the indicator member 302c by a relatively large distance.

The foregoing has outlined features of several embodiments. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A wafer process chamber leak detector, comprising:
   a wafer process chamber;
   a gas supply line coupling a gas supply to the wafer process chamber, the gas supply line comprising a final valve located on the gas supply line between the gas supply and the wafer process chamber;
   an indicator member coupled to the gas supply line between the final valve and the wafer process chamber;
   a reflecting member located adjacent the indicator member;
   a signal amplifier operable to direct an initial light through the indicator member, receive a reflected light that results from the initial light reflecting off the reflecting member, compare the reflected light to the initial light, and produce an amplified signal related to a difference between the reflected light and the initial light; and
   a gas supply cut-off device coupled to the signal amplifier and operable to automatically prevent gas from being supplied to the wafer process chamber through the gas supply line in response to receiving the amplified signal from the signal amplifier.

2. The wafer process chamber leak detector of claim 1, wherein the wafer process chamber houses at least one wafer processing device.

3. The wafer process chamber leak detector of claim 1, wherein the gas supply comprises a helium gas.

4. The wafer process chamber leak detector of claim 3, wherein the indicator member comprises a Cobalt(II) Chloride indicator member that is operable to change color due to a reaction with water.

5. The wafer process chamber leak detector of claim 1, wherein the indicator member and the reflecting member are located within the wafer process chamber and the signal amplifier is located outside of the wafer process chamber.

6. The wafer process chamber leak detector of claim 5, further comprising:
   a section on the wafer process chamber that allows the light from the signal amplifier to pass through such that the light can reach the indicator member and the reflecting member and be reflected back to the signal amplifier.

7. The wafer process chamber leak detector of claim 1, wherein the coupling of the indicator member to the gas supply line between the final valve and the wafer process chamber provides for real-time monitoring of gas supply line leaks within the wafer process chamber.

8. A wafer process chamber leak detector, comprising:
   a wafer process chamber housing a wafer support device;
   a gas supply line coupling a gas supply to the wafer support device and operable to supply a gas to a wafer located on the wafer support device;
   an indicator member coupled to the gas supply line between the gas supply and the wafer support device;
   a final valve located on the gas supply line between the gas supply and the indicator member, wherein there are no valves located on the gas supply line between the final valve and the indicator member and there are no valves located on the gas supply line between the indicator member and the wafer support device;
   a reflecting member located adjacent the indicator member;
   an emitter operable to direct an initial light through the indicator member in order to be reflected off the reflecting member to provide a reflected light;
   a receiver operable to receive the reflected light;
   a signal amplifier operable to compare the reflected light to the initial light and produce an amplified signal related to a difference between the reflected light and the initial light; and
   a gas supply cut-off device coupled to the signal amplifier and operable to automatically prevent gas from being supplied to the wafer process chamber through the gas supply line in response to receiving the amplified signal from the signal amplifier.

9. The wafer process chamber leak detector of claim 8, wherein the wafer process chamber houses at least one wafer processing device.

10. The wafer process chamber leak detector of claim 8, wherein the gas supply comprises a helium gas.

11. The wafer process chamber leak detector of claim 10, wherein the indicator member comprises a Cobalt(II) Chloride indicator member that is operable to change color due to a reaction with water.

12. The wafer process chamber leak detector of claim 8, wherein the indicator member and the reflecting member are located within the wafer process chamber and the emitter and receiver are located outside of the wafer process chamber.

13. The wafer process chamber leak detector of claim 12, further comprising:
   a section on the wafer process chamber that allows the light from the emitter to pass through such that the light can reach the indicator member and the reflecting member and then be reflected back to the receiver.

14. The wafer process chamber leak detector of claim 8, wherein the coupling of the indicator member to the gas supply line between the final valve and the wafer support device provides for real-time monitoring of gas supply line leaks within the wafer process chamber.

* * * * *